United States Patent [19]
Clarke et al.

[11] 3,945,834
[45] Mar. 23, 1976

[54] AQUEOUS COMPOSITIONS FOR LUMBER TREATMENT

[75] Inventors: Michael R. Clarke; Raman Desai, both of Ottawa, Canada

[73] Assignee: Canadian Patents and Development Limited, Ottawa, Canada

[22] Filed: May 2, 1973

[21] Appl. No.: 356,355

[30] Foreign Application Priority Data
Sept. 1, 1972 Canada................................ 150792

[52] U.S. Cl.................... 106/15 R; 21/7; 252/8.1; 252/193; 252/380; 260/29.6 MN; 260/29.7 N; 427/331
[51] Int. Cl.².... B27K 3/32; B27K 3/52; C09D 5/14
[58] Field of Search....... 106/15 AF; 117/147; 21/7; 260/29.6 MN; 424/145

[56] References Cited
UNITED STATES PATENTS

| | | | |
|---|---|---|---|
| 2,414,661 | 8/1943 | Nikitin | 106/15 AF X |
| 2,573,252 | 10/1951 | Farber | 106/15 AF X |
| 3,502,777 | 3/1970 | Burkhardt et al. | 21/7 X |
| 3,523,049 | 8/1970 | Putman | 21/7 X |

FOREIGN PATENTS OR APPLICATIONS

| | | | |
|---|---|---|---|
| 568,393 | 1/1959 | Canada | 106/15 AF |

Primary Examiner—Lucille M. Phynes
Attorney, Agent, or Firm—Flynn & Frishauf

[57] ABSTRACT

A wood treating composition is provided, comprising an aqueous solution containing (a) a specified amount of a water insoluble zinc compound, namely zinc carbonate, zinc oxide or zinc thiocyanate; (b) one of (i) a specified amount of ammonium thiocyanate, or (ii) a specified amount of ammonium carbonate, or (iii) a specified amount of both ammonium thiocyanate and ammonium carbonate; and (c) a specified amount of a zinc compound solubilizing amount of ammonia, the composition having a pH of 9 or more. The components may be provided by dissolving ZnO in an aqueous ammonia solution containing carbonate ions, or by dissolving zinc carbonate in an aqueous ammonia, or by means of an aqueous ammoniacal solution of $Zn(CNS)_2$. The composition may also include one or more of the following: (a) cupric ammonium ions, (b) a vinyl polymer latex, (c) optionally, an acidic organic surfactant compound which is soluble in said ammoniacal salt solution, or (d) an additional fungicidal agent.

10 Claims, 6 Drawing Figures

AQUEOUS COMPOSITIONS FOR LUMBER TREATMENT

RELATED INVENTION

This application is related to copending application Ser. No. 362,104, filed May 27, 1973, directed to arsenic-containing wood treating compositions.

BACKGROUND OF THE INVENTION

1. Field of the Invention

This invention relates to compositions and procedures for the treatment of wood and wood products, for protection during storage and handling of the lumber, or as a primer of sheathing. It also relates to the treated wood produced so formed.

2. Description of the Prior Art

A piece of timber, due to the manner of its formation, possesses anisotropic structure which influences its properties and behaviour. Compared to competitive cladding materials, for example metals and plastics materials, it has a number of major disadvantages which tend to counteract the advantages of strength, lightness, low thermal expansion and desirable aesthetic features. To overcome and minimize these disadvantages a number of specific problems exist: the wood must be protected against degrading environmental factors (namely, moisture cycling, photodegradation and biological attack); the dimensional stability with respect to moisture cycling must be improved; photodegradation due to sunlight must be minimized; the resistance to biological attack (fungus) must be improved; the adhesion of protective and decorative coatings must be improved; and extractives which adversely affect protective and decorative properties of coatings must be sealed within the wood. All these aims should be achieved with a treatment that does not alter the natural beauty of wood.

Four classes of treatments are currently used in an attempt to meet these requirements.

The first class is that of clear or pigmented penetrating systems which contain fungicides and water-repellent additives, such as, for example, polyethylene waxes and metal stearates in a non-aqueous solvent media. These treatments are deficient in that they must be repeated at regular intervals of 1 to 2 years to provide a desired level of protection.

The second class is that of stains and sealers. These are normally synthetic resin solutions, usually pigmented and designed to penetrate the surface of the wood. These treatments as well are deficient, and should be repeated every one or two years in order to provide the required degree of protection.

The third class is that of paint systems. Such paint systems would normally consist of a primer and top coats. When well applied, these will provide the exterior cladding protection from two to five years.

The fourth class is that of salt treatments. A number of salt treatments have been suggested, the most common of which are known as copper-chrome arsenate (CCA) and acid-copper-chromate (ACC). Presently systems of this type are effective to provide relatively long term durability when applied by pressure impregnation techniques. The CCA systems are believed to become fixed in the wood by oxidation-reduction reactions associated with the chromic acid in the compositions and it is these same reactions which are believed adversely to affect stability and processing characteristics. Moreover, while providing a high level of protection against fungal attack, they provide only limited protection against weathering.

Coper and zinc containing fungicides have been proposed (see U.S. Pat. No. 2,414,661 issued Jan. 21, 1947 to A. A. Nikitin) which were prepared by precipitation from an aqueous solution of a zinc salt and a copper salt with an alkali solution containing soya bean protein, or soaps of fatty acids.

Fungicides have been proposed for cellulosic materials (see U.S. Pat. No. 2,423,619 issued July 8, 1947 to L. Roon) which comprise copper soaps formed in situ from an aqueous solution of copper salts and aqueous ammonia by reaction with fatty acids.

It has also been proposed to provide water and fire resistant coatings on wood (see U.S. Pat. No. 2,530,458 issued Nov. 21, 1950 to H. R. Frisch) by the use of zinc orthophosphate or zinc orthoarsenate compositions applied as a concentrated solution in aqueous ammonia. Zinc arsenate, zinc arsenite, and zinc phosphate can all be applied from ammonia solution and, on drying, the salt is insoluble and fixed in the wood. However, in all of these cases the weather resistance of the treated wood is not signficantly improved.

It was proposed to improve the hardness, compressive strength hygroscopicity and liability to swell of wood by impregnating the wood with an aqueous ammoniacal solution of polycarboxylic acid containing aT least 6 carbon atoms. (See U.S. Pat. No. 2,768,910 issued Oct. 30, 1956 to H. Krzikalla and O. Lissner).

U.S. Pat. No. 2,772,263 issued Nov. 27, 1956 to C. C. Yeager proposed to use a compound having a high fungicidal activity in wood, which is a metal rosin ammonium phenoxide, prepared by reacting a rosin ammonia phenoxide with a water soluble salt of a metal capable of forming a complex with ammonia.

U.S. Pat. No. 3,007,844 issued Nov. 7, 1961 to W. O. Schuly proposed the use of a composition comprising a heavy metal ion, borate ions and chromate ions as an impregnating agent for the preservation of wood.

U.S. Pat. No. 3,105,773 issued Oct. 1, 1963 to S. Frank and D. C. Wehner proposed to preserve wood by imparting pesticidal and anti-thallophytic properties by first impregnating the wood with a water soluble heavy metal salt, and then with an acrylic polymer solution.

Ammoniacal copper arsenite compositions are present being used as preservatives.

AIMS OF THE INVENTION

While the use of the compositions outlined above provided a considerable level of protection against weathering and biological attack and effectively sealed the wood and improved the adhesion of paints applied to the treated wood, the level of weather resistance achieved fell short of what was required to being the durability of wood to a level competitive with other cladding materials. None of such systems provided a suitable balanced improvement in the following requirements, namely: to impart long life to the treated wood product; to provide protection without reducing the natural appearance of the treated wood; to be capable of being applied by simple (low cost) methods of application (for example, low pressure application); and to expand the applicability of these systems which would not impart a strong colour to the treated wood. A large amount of effort has therefore been expanded in modifying formulations to impart acceptable colour to the treated wood.

Therefore, prime objectives of this invention are to provide such compositions in which a suitable balanced improvement, namely for periods up to one year, is provided in the following properties, namely: a good level of weather resistance; low mammalian toxicity; fire retardant characteristics; resistance to biological and fungal attack; resistance to water penetration; resistance to extractive staining; adhesion properties between the wood and a coating, e.g. paint or glue, etc. later to be applied thereto; a mill treatment procedure; and no substantial adverse effect on lumber seasoning.

SUMMARY OF THE INVENTION

Broad Statements of the Invention

By one broad aspect of this invention, a wood treating composition is provided containing: (a) a water insoluble zinc compound, selected from the group consisting of zinc carbonate, zinc oxide and zinc thiocyanate, in a total amount, in the solution, of about 0.5 to about 10% by weight, as zinc; (b) one of (i) ammonium thiocyanate, in an amount of about 1 to about 28% by weight, with the mole ratio calculated as $(NA_4CNS)/ZnO$ being from about 2 to about 3, or (ii) ammonium carbonate, in an amount of about 0.5 to about 15% by weight, with the mole ratio calculated as $[(NH_4)_2CO_3]/ZnO$ being from about 1 to about 1.5, or (iii) both ammonium thiocyanate and ammonium carbonate, in an amount of about 1 to about 28% by weight, with the mole ratio calculated as $(NH_4CNS+(NH_4)_2CO_3/ZnO$ being from about 1 to about 3; and (c) a zinc salt dissolving amount of ammonia, in an amount of about 0.3 to about 28%, sufficient to provide a ratio of ammonia to zinc of at least about 0.3 to about 1, the composition having a pH of about 9 or more.

VARIANTS OF THE INVENTION

Such composition may be provided by the following solutions:

1. ZnO dissolved in an aqueous ammonia solution containing carbonate ions, preferably wherein the amount of ZnO is about 0.5 to about 10% by weight, and the aqueous ammonia solution is at a concentration of about 1 to about 28% by weight, and with the amount of $NH_3$ being correlated to the amount of ZnO to provide a mole ratio of $NH_3$ to Zn of at least about 0.3 to about 1, and the amount of ammonium carbonate ions being about 0.5 to about 15% by weight, with the mole ratio of $(NH_4)_2CO_3$ to ZnO being from about 1 to about 1.5.

2. A solution of zinc carbonate in aqueous ammonia, preferably wherein the amount of zinc carbonate is about 0.75 to about 15% by weight and the aqueous ammonia is at a concentration of about 1 to about 28% by weight, with the mole ratio of ammonium carbonate to zinc carbonate (expressed as zinc oxide) being about 1 to about 1.5.

3. An aqueous ammoniacal solution of $Zn(CNS)_2$, preferably wherein the amount of $Zn(CNS)_2$ is about 1 to about 25% by weight, and the aqueous ammonia is at a concentration of about 1 to about 28% by weight, with the mole ratio of ammonium thiocyanate to zinc thiocyanate (expressed as zinc oxide) being about 2 to about 3.

By another aspect of this invention, a first modified composition includes, additionally, copper, as cupric ammonium ions, preferably in the proportion of about 30% by weight (based on the amount of zinc present) although lesser amounts of copper will still provide some benefits. Such cupric ammonium ions may be provided by dissolving copper oxide or copper carbonate in the ammoniacal zinc salt solution.

By another aspect of this invention, a second modified composition is provided in which the principal composition, or the first modified composition includes, additionally, up to about 10% by weight (total) of a vinyl polymer latex.

By yet another aspect of this invention, a third modified composition is provided in which the principal composition, or the first modified composition or the second modified composition includes, additionally, up to about 30% by weight (based on the amount of zinc present) of an acidic organic surfactant compound which is soluble in the ammoniacal salt solution.

By still another aspect of this invention, a fourth modified composition is provided, in which the principal composition, or the first, second or third modified composition includes, additionally, up to about 30% by weight (based on the amount of zinc present) of an additional fungicidal agent.

If the composition is to be used as a sealer primer, the presence of a surfactant is not necessary. However, the presence of suitable surfactants or wetting agents is of great importance in the application of these compositions by continuous spray application. Such continuous movement lines on which these treatments are carried out can move at a rate up to about 1200 feet a minute. The surfactants which are suitable for use in these compositions generally may be described as acidic organic compounds which are insoluble in water but which are solubilized by the ammoniacal salt solution. They are used to improve the wetting characteristics of the composition on wood and, where latex is also present, they are used to improve the stability of the polymer dispersion. These acidic organic compounds generally comprise aliphatic or aromatic compounds or halogenated derivatives thereof. The aliphatic compound generally has chains or loops of a length of about 10 to about 18 carbon atoms between acid groups. They may have complex structures in which there is more than one acidic group. Examples of such mterials include the following: an ester of phosphoric acid, decanoic acid, a phenol, a chlorinated phenol, or a dimer acid formed from unsaturated fatty acids. Such surfactants will normally be present in solution as the salt of the zinc ammonia complex. In some cases, it may be desirable first to prepare a zinc salt of the organic acid before adding it to the composition. If a latex is present, the surfactant is generally added to the latex and then the two solutions are mixed. Unlike other compositions without latex, formulations containing the latex will require larger quantities of the surfactant, depending on the type of latex used.

Another optional ingredient in the composition of an aspect of this invention is a latex, which may be used to enhance the effectiveness of this composition. The latex generally has fine particle size, about 0.01 to about 0.1 microns, and a glass transition temperature below about +5°C. The chemical composition is such that the latex would form water repellent films and would be insolubilized on drying by reaction with the salt composition. They are, in general, vinyl polymer latices produced from monomers such as, for example, styrene, vinyl acetate, acrylic and methacrylic monomers. Preferably, the vinyl polymer is a copolymer of acrylic acid, methacrylic acid, acid esters of maleic acid, itaconic acid or acid esters of itaconic acid, as well as styrene-butadiene copolymers. Thus, for example, they include copolymers of styrene, vinyl acetate, acrylic monomer or methacrylic monomer with acrylic acid, methacrylic acid, acid esters of maleic acid, itaconic acid or acid esters of itaconic acid, or styrene-butadiene polymers or 2-ethylhexyl acrylate polymers.

For applications of this composition for protection of lumber during air-seasoning and in storage or transit, an additional fungicide may be added to enhance the fungicidal activity of the zinc itself or of the optionally added copper. The fungicides are characterized in that they are capable of forming insoluble salts or complexes with the zinc salts of the composition. They are used at levels which do not detract from the water repellent characteristics of the salt composition. Examples of these include hexamine (hexamethylenetetramine), chlorinated phenols, acids of arsenic, dimethylthiocarbamate, ammonium hydrosulfite, ethylenebisthiocarbamate and ammonium thiocyanate.

In one procedure for preparing the composition of an aspect of this invention, a concentrated solution of ZnO and strong $NH_3$ with the requisite amount of $(NH_4)_2CO_3$ is prepared. Such concentrated solution is then diluted with water to obtain the desired concentration. If desired, the surfactant is then added to this composition in appropriate quantities.

The level of ammonia used in the above formulations is generally in excess of that required to form salts or coordinating complexes so that the aqueous compositions will have a pH of about 9 or higher. In addition the ratio of ammonia to zinc should be at least about 0.3 to about 1. The non-volatile solids of the compositions may vary between about 2% and about 60%.

While it is not desired to be limited to any particular theory, it is believed that the high moisture pick-up of wood is due to physical absorption of moisture onto cellulose chains in the microfibrils, resulting in a decrease in the association between neighbouring cellulose chains. It is felt that the improvement in moisture pick-up of the treated wood is due to a cross-linking action by the metal ion between neighbouring cellulose chains. This cross-linking action could occur due to the high strength of coordination linkages. It is further believed that resistance to photodegradation is associated with the formation of pigment crystals formed within the wood substance which effectively screens the natural polymers from the damaging radiation.

BRIEF DESCRIPTION OF THE DRAWINGS

In the accompanying drawings.

DESCRIPTION OF THE EXAMPLES OF THE INVENTION

Figure 1:
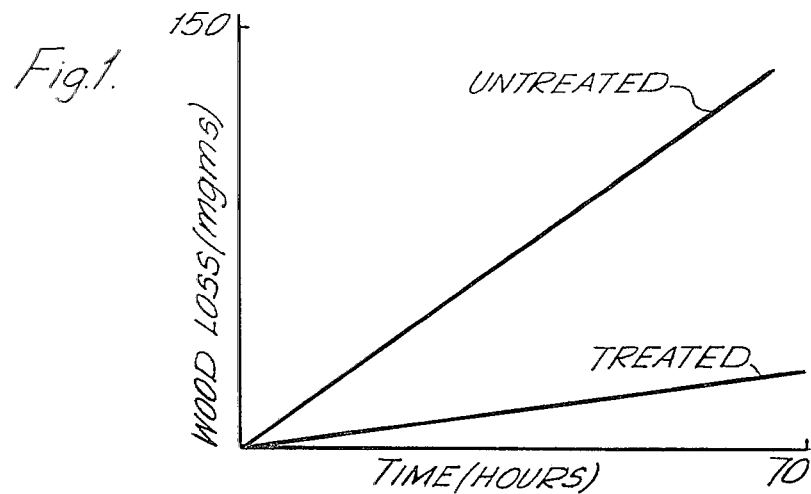
FIG. 1 is a graph showing the light stability of treated and untreated wood, with wood loss (in mgms) as ordinate and time (in hours) as abscissa.

The invention in certain of its embodiments is illustrated in the following examples in which all proportions are by weight.

EXAMPLE 1

Moisture Pickup

A treating solution according to one embodiment of this invention was prepared as follows: Zinc oxide and ammonium carbonate were mixed with concentrated (28%) aqueous ammonia solution and stirred to effect solution. Water was then added to achieve the following formulation:

| | |
|---|---|
| zinc oxide | 5 parts |
| ammonium carbonate | 5 parts |
| aqueous ammonia solution (5%) | 90 parts |

White spruce and white pine panels 2 × 8 × ½ inches were used in this example.

Matched pairs of panels were cut from the same piece of lumber. One of these was subjected to treatment and the other was used as a control specimen.

The treating solution was applied to the panels by three processes: (1) by spray; (2) by brush; and (3) by a 10 second dip.

Treated samples and controls were subjected to a 6 hour water spray in a Xenon Weather-Ometer. The moisture pickup on treated specimens was less than half that obtained with the untreated controls.

EXAMPLE 2

A treating solution according to one embodiment of this invention was prepared using the procedure described in Example 1, to provide a composition having the following formulation:

| | |
|---|---|
| zinc oxide | 9 parts |
| ammonium carbonate | 9 parts |
| copper carbonate | 1 part |
| aqueous ammonia (10%) | 81 parts |

Wood samples similar to those used in Example 1 were used in this Example.

The samples to be treated were pre-heated to a surface temperature of 100°C. They were then dipped for 10 seconds into the cold treating solution.

A. Moisture Pickup

Treated samples and untreated samples (controls) were subjected to a water spray for 6 hours.

The moisture pickup in the treated samples was less than 50% of that of the controls.

B. Erosion Resistance

Treated and untreated (control) samples were subjected to ultraviolet radiation using a mercury diffusion lamp placed 5 inches from the surface of the sample for a period of 80 hours.

The control samples suffered erosion of the surface to a depth of 1/32 to 1/16 in. in the springwood bands. No erosion was observed with the treated specimens.

C. Fungal Resistance

Treated and untreated (control) samples were inoculated with spores of the following fungi: Neurospora, *Aspergillus niger* and a mixture of molds (Neurospora, Penicillium and *Ceratacystis adiposa*).

The control samples showed growth of the fungi within 1 week. Treated samples showed no mold growth.

EXAMPLE 3

Moisture Pickup

A treating solution according to one embodiment of this invention was prepared using the procedure described in Example 2 to give the following formulation:

| | |
|---|---|
| zinc oxide | 5 parts |
| ammonium carbonate | 5 parts |
| AC61 (Trade Mark of Rohm & Haas for its acrylic latex) (20% solids) | 50 parts |
| aqueous ammonia (10%) | 40 parts |

Wood samples used in this Example were similar to those described in Example 1.

Test Method (A)

The samples to be treated were pre-heated to a surface temperature of 100°C. using infrared radiation and then were given two passes through a roller coater where the treating solution was applied (the application roll of the roller coater was covered by a lambs wool sleeve).

Test Method (B)

Samples to be treated were placed in a pressure vessel and were evacuated for 20 minutes. The treating solution was then introduced to the pressure vessel sufficient to cover the specimens to be treated. An over pressure of 100 lbs/sq. in. of air was applied and this pressure was maintained for 3 hours. The pressure in the treating vessel was then reduced to atmospheric pressure and the treating solution was removed.

Samples treated by method (A) and method (B) described above and control samples were subjected to 6 hours water spray in a Xenon Weather-Ometer. Regardless of the method of treatment, the moisture pickup of the treated samples was less than 50% of the moisture pickup of the control samples.

EXAMPLE 4

Wet Strength Increase of Paper

A treating solution according to one embodiment of this invention was the same as was used in Example 1. The sample tested was Whatman No. 1 filter paper (unsized). The paper was dipped for 1 second into the treating solution and dried.

Samples of treated paper and untreated paper were cut in size 0.5 inch × 5 strips and the wet tensile strength (in the machine direction) was determined according to Tappi Standards Method T456-OS68 for tissue products.

The wet strength of the treated paper was increased by 700 percent over that of the untreated paper. The average wet strength of the treated paper was 2.2 lb. as compared to 0.3 lb. for the untreated paper. This was equal to 33 percent of the dry strength of the untreated paper (6.5 lbs.).

EXAMPLE 5

Light Stability

The treating solution according to one embodiment of the present invention was an aqueous composition having the following formulation: ZnO, 5%; $(NH_4)_2CO_3$, 6%; $NH_3$, 14%; decanoic acid, 0.2%. Spruce and pine panels, dipped in the solution, showed marked increase in the light resistance and water repellency of the treated panel as compared to untreated panels.

This is shown graphically in FIG. 1.

EXAMPLE 6

Siding Application as a Primer

The treating solution of one embodiment of the present invention as used herein was an aqueous composition having the following formulation: ZnO, 5%; $(NH_4)_2CO_3$, 6%; $NH_3$, 3.5%; latex (small particle size butadiene-styrene latex), 5%; decanoic acid, 0.5%. The composition was applied to western red cedar panels as a primer-sealer and then the panels were top coated with a conventional exterior paint. Control panels were primed with diluted conventional exterior latex paint and then top coated with the same paint. After 200 hours in a Xenon Weather-Ometer, extractive staining was evident on the controls while no staining occured with panels primed with the composition of this invention.

EXAMPLE 7

Fire Retardancy

The treating solution of one embodiment of the present invention as used herein was an aqueous composition having the following formulation: ZnO, 14.5%; $(NH_4)_2CO_3$, 15.5%; $NH_3$, 10%; decanoic acid, 0.1%. Pine panels sprayed with this composition exhibited substantial reduction in flame spread index as compared to untreated panels.

EXAMPLE 8

Control of Kiln Burn

The treating solution of one embodiment of the present invention as used herein was an aqueous composition having the following formulation: ZnO, 1%; $(NH_4)_2CO_3$, 1.2%; $NH_3$, 2.5%; decanoic acid, 0.1%. Dip treatment of green white pine boards almost completely eliminated the brown stain conventionally produced during kiln drying of the boards. The results are shown below in the following table.

| Effect of Ammoniacal Zinc Oxide on Number of White Pine Boards with Brown Stain after Kiln Drying | | | | |
|---|---|---|---|---|
| Percent of Surface Stained | Rough | | Skip Planed | |
| | Treated | Controls | Treated | Controls |
| 0 | 34 | 1 | 38 | 1 |
| 0 – 24 | 6 | 4 | 2 | 17 |
| 25 – 49 | 0 | 11 | 0 | 9 |
| 50 or more | 0 | 24 | 0 | 13 |

EXAMPLE 9

Reduction of Fungal Staining in Seasoning and Lumber Transit

The treating solution of one embodiment of the present invention as used herein was an aqueous composition having the following formulation: ZnO, 5%; $(NH_4)_2CO_3$, 6%; $NH_3$, 3.5%; decanoic acid, 0.1%. Green pine skip-planed boards were dipped in the solution and sprayed with spores of fungi. These and matching controls were then placed in a tropical chamber (95% relative humidity at 70°F.) for 12 days and examined for mold and stain fungi growth. Molds and fungi grew luxuriantly on the controls while the treated boards were practically free from molds and fungal attack.

These results are shown below in the following two tables:

Effect of Treating Solution of the Invention on Number of White Pine Boards with Fungal Discolorations after Air-Seasoning

| Amount of Staining | Treated | Controls |
|---|---|---|
| None | 17 | 1 |
| Very slight | 11 | 9 |
| Slight | 7 | 10 |
| Moderate | 1 | 13 |
| Heavy | 0 | 3 |

Effect of Treating Solution of the Invention on Number of Skip-Planed White Pine Boards With Yellow Stain After Air-Seasoning

| Amount of Staining | Treated | Controls |
|---|---|---|
| None | 22 | 1 |
| Very slight | 12 | 3 |
| Slight | 2 | 11 |
| Moderate | 0 | 14 |
| Heavy | 0 | 7 |

EXAMPLE 10

Water Repellency

Figure 2:
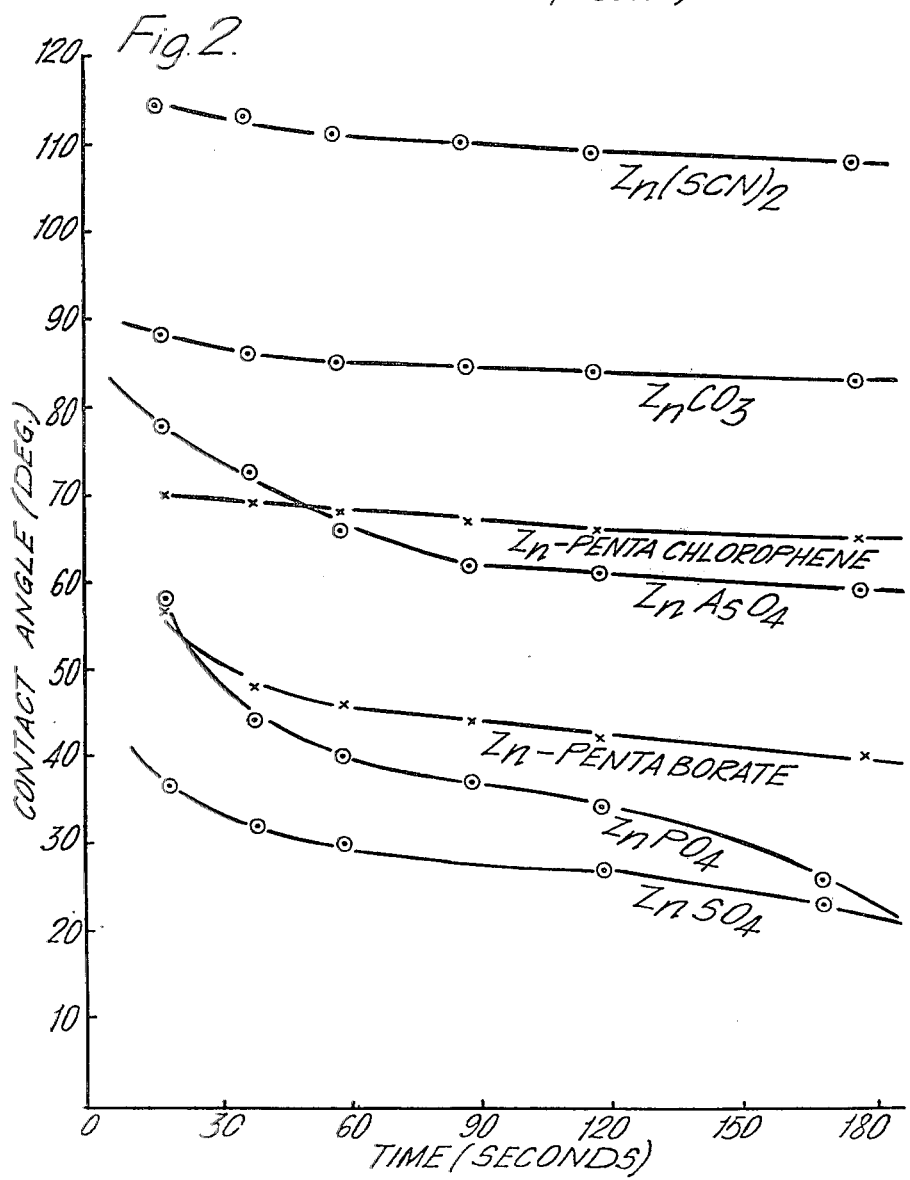
FIG. 2 is a graph showing the contact angles of water on treated spruce, treated with various compositions, with contact angle (in degrees) as ordinate and time (in seconds) as abscissa.

The unexpected improvement in water repellency was determined by measuring the contact angle of various treated spruce panels. (The contact angle is a measure of water repellency, and is the term applied to the angle formed by water on the surface of a solid at the gas-solid-liquid interface, measured as the dihedral angle in the liquid.) The panels were treated with the following treating solutions: $Zn(SCN)_2$; $ZnCO_3$; zinc pentachlorophenol; $ZnAsO_4$; zinc pentoborate; $ZnPO_4$; and $ZnSO_4$. The results are shown graphically in FIG. 2.

It is seen that the treating composition of aspects of this invention has a surprising and unexpectedly much greater contact angle than the analogous treating agents of the prior art.

EXAMPLE 11

Water Pickup on Spruce, Pine and Western Red Cedar

Figure 3:
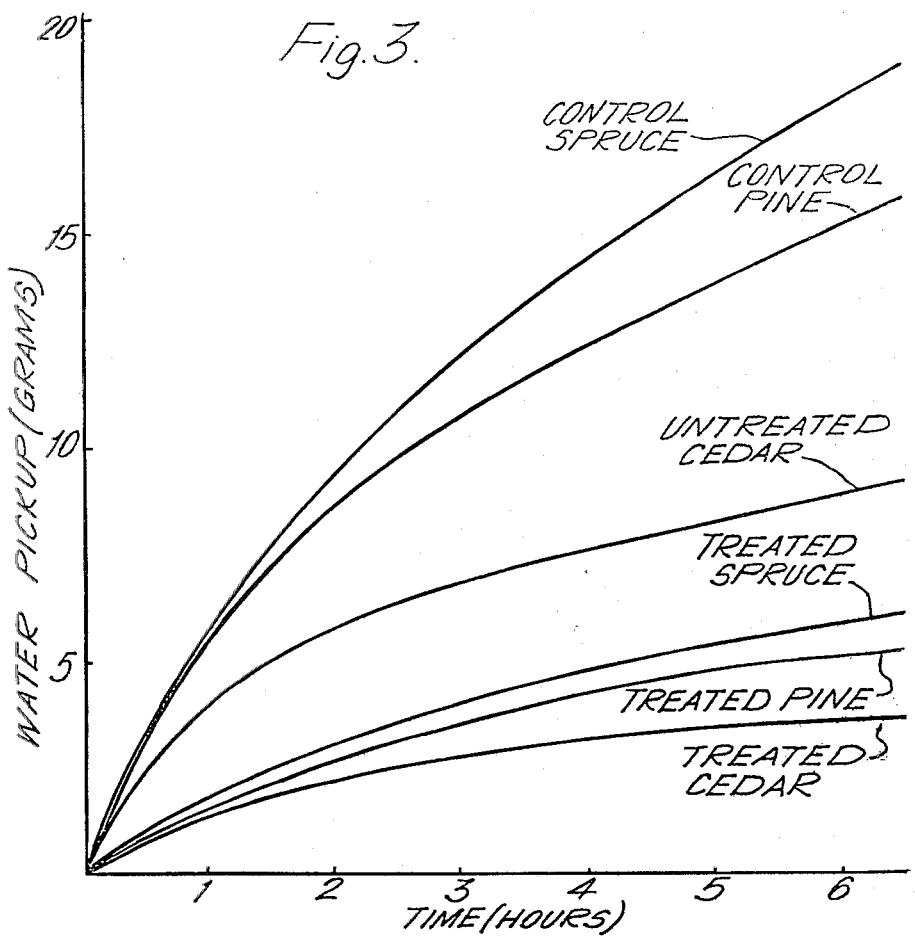
FIG. 3 is a graph showing water pick-up on spraying on treated and untreated spruce, pine and cedar, with water pick-up (in grams) as ordinate and time (in hours) as abscissa.

Tests were also-conducted on panels of spruce, pine and western red cedar, some of which had been treated with the treating composition of embodiments of this invention, and some of which were untreated, for controls and the amount of liquid water uptake in a Xenon Weather-Ometer was determined. It is seen from the graph in FIG. 3 that in 6 hours, the treated western red cedar panels took up approximately one-half as much water as the untreated, control panels and that the water takeup of treated spruce and treated pine is much less than that of untreated spruce and pine, respectively, and is even less than untreated cedar.

EXAMPLE 12

Water Pickup with Latex-containing Composition

Figure 4:
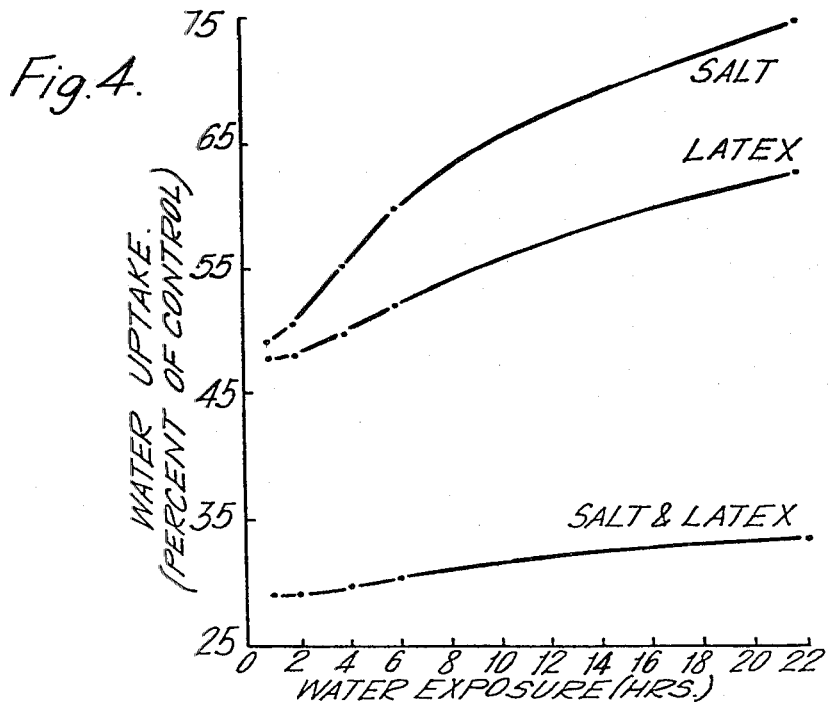
FIG. 4 is a graph showing resistance to water uptake, on a spruce substrate of various compositions, with water uptake (as percentage of control) as ordinate, and water exposure (in hours) as abscissa.

The synergistic effect of the composition of another embodiment of this invention with, additionally a latex (e.g. a butadiene-styrene latex) was ascertained by determining the water takeup of a sample treated with the composition of this invention, and of a sample treated with the latex alone, and of a sample treated with the composition of this invention with, additionally, latex, as well as untreated control panels. The results are shown graphically in FIG. 4.

It is seen that while the panel treated with the composition of this invention took up about 75% of that taken up by the control, and while the latex treated panel took up about 60% of that taken up by the control, the composition of this invention with, additionally, the latex, took up only about 30%.

EXAMPLE 13

Fire Retardancy

Another desirable characteristic imparted to the wood by the treating composition of aspects of this invention is fire retardancy, indicated by decreased weight loss on ignition and by improved flame spread index.

Figure 5:
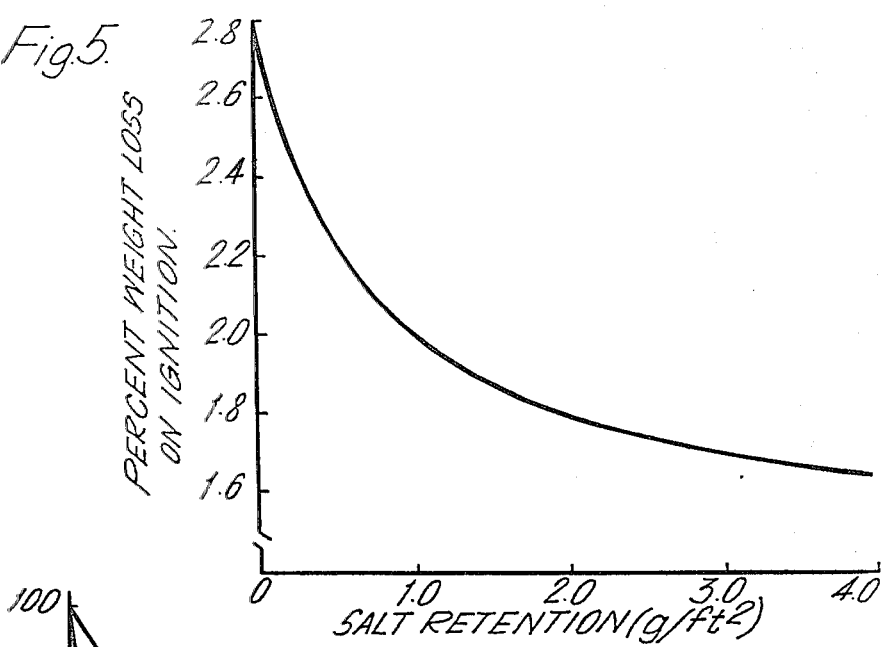
FIG. 5 is a graph showing an indication of fire retardancy, on treated white pine, with percent weight loss in ignition as ordinate, and salt retention (in grams/ft$^2$) as abscissa.

As shown in FIG. 5, as the salt retention due to treatment with the composition of aspects of this invention of white pine by dipping increases to 4.0 g/ft$^2$, the percent weight loss on ignition drops dramatically.

Figure 6:
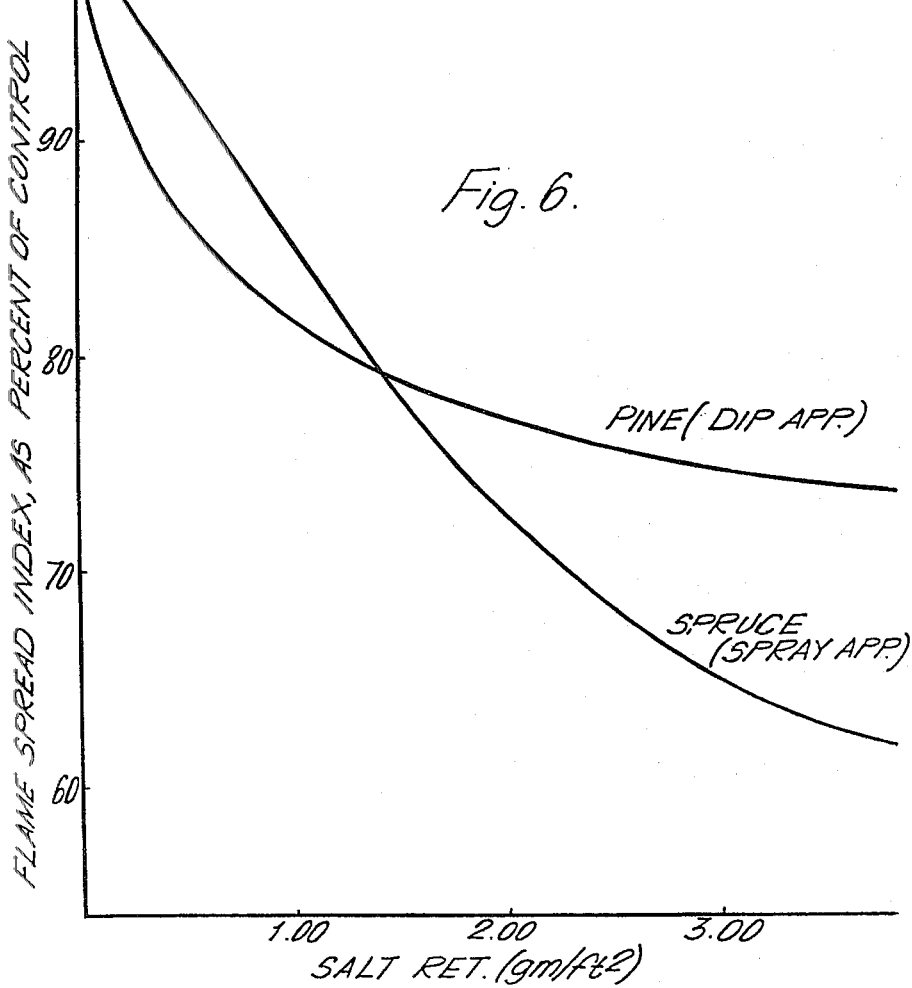
FIG. 6 is a graph of flame spread index of treated white pine and treated spruce, with flame spread index as percent of control as ordinate, and salt retention (in grams/ft$^2$) as abscissa.

As shown in FIG. 6, the flame spread index is reduced proportionally to the amount of salt retained in the white pine or spruce panels treated with the composition of aspects of this invention. In the pine panels, for a salt retention of 4.00 g/ft$^2$ the flame spread index is only about 75% of that of the control pine panel. For spruce panels, for a salt retention of 3.00 g/ft$^2$, the flame spread index is only abut 65% of that of the control spruce panel.

EXAMPLE 14

Lumber Seasoning

It was also determined that there was no adverse effect on lumber seasonings by determining the loss in moisture on drying white pine treated with the composition of aspects of this invention. The results, comparing control panels with treated panels, are summarized below.

| | Percent Loss in Moisture on Oven Drying White Pine | | | | | |
|---|---|---|---|---|---|---|
| | Board No. 1 | | Board No. 2 | | Board No. 3 | |
| Drying Time (hrs) | Control | Treated | Control | Treated | Control | Treated |
| 6 | 6.42 | 5.73 | 6.32 | 5.90 | 4.03 | 4.06 |
| 22 | 23.55 | 23.39 | 24.41 | 27.01 | 16.27 | 25.63 |

-continued

| Drying Time (hrs) | Percent Loss in Moisture on Oven Drying White Pine | | | | | |
|---|---|---|---|---|---|---|
| | Board No. 1 | | Board No. 2 | | Board No. 3 | |
| | Control | Treated | Control | Treated | Control | Treated |
| 28 | 28.27 | 28.49 | 31.72 | 31.26 | 24.09 | 29.92 |
| 72 (oven dry) | 52.54 | 53.05 | 60.99 | 60.95 | 54.18 | 54.82 |

COMPARATIVE TESTS

Comparative tests were carried out following the teachings of U.S. Pat. Nos. 2,423,619; 2,414,661; and 2,423,616.

EXAMPLES OF TREATING WOOD WITH COPPER AND ZINC SOAPS

Copper and zinc soap solutions in ammonia were prepared as directed in U.S. Pat. No. 2,423,619 and wood sample were brushed with the solutions. The samples were then top-coated with a conventional exterior acrylic latex. A cross-hatch test indicated that samples brushed with zinc soap solutions adversely affected the adhesion of the latex to substrate. The copper soap solutions treated sample did not affect the adhesion appreciably.

In another experiment, brushed and top-coated cedar wood samples were subjected to high humidity gradients. Within two to three hours, the copper-soap treated samples were stained due to extractive bleed through while the zinc-soap treated samples blistered badly.

As a comparison, similar wood samples treated with the composition of this invention did not exhibit any bleed through of extractives or blistering over a period of six to eight hours under identical conditions. In addition, the adhesion of the latex top coat to the samples treated with the composition of this invention was good.

U.S. Pat. No. 2,414,661

The patent refers to insoluble metal soaps. As the proportions of the salts in the compositions of the present invention are defined in terms of zinc metal, the small concentrations of the ions left with the insoluble soaps taught in U.S. Pat. No. 2,414,661 provides a composition that does not possess the characteristics of the composition of the present invention.

U.S. Pat. No. 2,423,616

Applicants were unable to prepare the metal soap solutions as described in the patent in compositions according to the present invention. Stearic acid and oleic acid did not dissolve in large quantities in strong or dilute ammonia. One may be able to obtain solutions with ammounts below one percent only.

A composition has thus been provided in which the durability of the treated wood or wood product is vastly improved without necessarily modifying the natural appearance of the wood or wood product. However, formulation changes are permitted which will enable desired colour changes to be introduced. Compositions are provided in which compatible polymer/salt mixtures can be used which, on drying, are believed to cross-link within the wood substance and interact with the wood substance to provide still further enhanced characteristics.

The treatments using compositions of aspects of this invention confer the advantages indicated to the following range of wood products: lumber, shingles and shakes, plywood, particle-board, fiber boards, and paper products.

The preceding examples can be repeated with similar success by substituting the generically and specifically described reactants and operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

We claim:

1. A treating composition comprising an aqueous solution containing:
    a. a zinc compound, selected from the group consisting of zinc carbonate, zinc oxide and zinc thiocyanate, in a total amount, in the solution, of about 0.5 to about 10% by weight, as zinc;
    b. an ammonium composition consisting essentially of ammonium thiocyanate and ammonium carbonate, in an amount of about 1 to about 28% by weight, with the mole ratio calculated as $[NH_4CNS + (NH_4)_2CO_3]/ZnO$ being from about 1 to about 3; and
    c. ammonia, in an amount of about 0.3 to about 28%, sufficient to provide a ratio of ammonia to zinc of from at least about 0.3 up to about 1, the composition having a pH of 9 or more.

2. The wood treating composition of claim 1 including, additionally, copper ions.

3. The wood treating composition of claim 1 including, additionally, cupric ammonium ions, the proportion of said cupric ammonium ions being about 30% by weight (based on the amount of zinc present).

4. The wood treating composition of claim 1 including, additionally, cupric ammonium ions provided by dissolving copper oxide in the zinc salt solution.

5. The wood treating composition of claim 1 including, additionally, cupric ammonium ions provided by dissolving copper carbonate in the zinc salt solution.

6. The treating composition of claim 1 including in addition:
    d. not more than about 30% by weight (based on the amount of zinc present) of an acidic organic surfactant compound which is soluble in said ammoniacal salt solution.

7. The wood treating composition of claim 6 wherein said surfactant compound comprises an ester of phosphoric acid, decanoic acid, a phenol, a chlorinated phenol, or a dimer acid formed from an unsaturated fatty acid.

8. The treating composition of claim 1 including in addition:

e. not more than about 30% by weight (based on the amount of zinc present) of an additional fungicidal ingredient.

9. The wood treating composition of claim 8 wherein said additional fungicidal ingredient comprises hexamine, a chlorinated phenol, dimethylthiocarbamate, ammonium hydrosulfite, ethylene-bis-thiocarbamate, or an acid of arsenic.

10. A concentrated aqueous solution, containing a. a zinc compound, selected from the group consisting of zinc carbonate, zinc oxide and zinc thiocyanate, b. an ammonium composition consisting essentially of both ammonium thiocyanate and ammonium carbonate, the mole ratio $[(NH_4)_2CO_3 + NH_4CNS]/ZnO$ being about 1 to about 3; and c. ammonia, the mole ratio $NH_3/Zn$ being from at least about 0.3 up to about 1, and adapted, when diluted with water, to provide a wood treating composition as claimed in claim 1.

* * * * *

UNITED STATES PATENT AND TRADEMARK OFFICE
CERTIFICATE OF CORRECTION

PATENT NO. : 3,945,834
DATED : March 23, 1976
INVENTOR(S) : MICHAEL R. CLARKE et al It is certified that error appears in the above-identified patent and that said Letters Patent are hereby corrected as shown below:

Abstract, lines 18-19: replace "ammnoiacal" with
--- ammoniacal ---.

Column 2, line 4: replace "Coper" with --- Copper ---.

Column 2, line 24: replace "signficantly" with
--- significantly ---.

Column 2, line 28: replace "aT" with --- at ---.

Column 2, lines 34-35: replace "ammonia" with -- ammonium --.

Column 3, line 22: replace "($NA_4CNS$)" with --- ($NH_4CNS$) ---.

Column 3, line 31: after "$CO_3$", close parentheses (--- ) ---.

Column 7, line 8: replace "Ceratacystis" with
--- Ceratocystis ---.

Column 7, line 61: after "5", insert --- inch ---.

Column 9, line 51: replace "pentoborate" with -- pentaborate --.

Column 10, line 49: replace "abut" with --- about ---.

Column 11, line 21: replace "sample" with --- samples ---.

Column 11, line 57: replace "ammounts" with --- amounts ---.

UNITED STATES PATENT OFFICE
CERTIFICATE OF CORRECTION

PATENT NO. : 3,945,834
DATED : March 23, 1976
INVENTOR(S) : MICHAEL R. CLARKE et al It is certified that error appears in the above-identified patent and that said Letters Patent are hereby corrected as shown below:

Abstract, line 3 - replace "zine" with -- zinc --.

Column 2, line 55 - replace "being" with -- bring --.

Column 4, line 44 - replace "mterials" with -- materials --.

Column 8, line 32 - replace "occured" with -- occurred --.

Signed and Sealed this

Nineteenth Day of October 1976

[SEAL]

Attest:

RUTH C. MASON
Attesting Officer

C. MARSHALL DANN
Commissioner of Patents and Trademarks